(12) United States Patent
McClintock et al.

(10) Patent No.: US 8,282,642 B2
(45) Date of Patent: Oct. 9, 2012

(54) CERVICAL DRILL GUIDE APPARATUS

(75) Inventors: Larry McClintock, Gore, VA (US);
Peter Harris, Leesburg, VA (US); Todd Wallenstein, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 453 days.

(21) Appl. No.: 11/895,216

(22) Filed: Aug. 23, 2007

(65) Prior Publication Data
US 2008/0077152 A1  Mar. 27, 2008

Related U.S. Application Data

(60) Provisional application No. 60/847,593, filed on Sep. 26, 2006.

(51) Int. Cl.
*A61B 17/68* (2006.01)
*A61B 17/58* (2006.01)
(52) U.S. Cl. ........................ 606/86 B; 606/96
(58) Field of Classification Search ............... 606/96, 606/281, 79–80, 86 R, 86 B, 97, 104
See application file for complete search history.

(56) References Cited

U.S. PATENT DOCUMENTS

| 5,423,826 | A | 6/1995 | Coates et al. | |
|---|---|---|---|---|
| 5,676,666 | A | * 10/1997 | Oxland et al. | 606/86 B |
| 5,769,856 | A | 6/1998 | Dong et al. | |
| 5,851,207 | A | 12/1998 | Cesarone | |
| 5,895,390 | A | 4/1999 | Moran et al. | |
| 6,066,142 | A | 5/2000 | Serbousek et al. | |
| 6,241,729 | B1 * | 6/2001 | Estes et al. | 606/86 R |
| 6,379,364 | B1 * | 4/2002 | Brace et al. | 606/96 |
| 6,447,512 | B1 | 9/2002 | Landry et al. | |
| 6,524,312 | B2 * | 2/2003 | Landry et al. | 606/86 A |
| 6,616,671 | B2 * | 9/2003 | Landry et al. | 606/99 |
| 6,666,866 | B2 * | 12/2003 | Martz et al. | 606/86 A |
| 6,692,503 | B2 * | 2/2004 | Foley et al. | 606/96 |
| 7,037,311 | B2 | 5/2006 | Parkinson et al. | |
| 7,081,119 | B2 | 7/2006 | Stihl | |
| 7,094,242 | B2 | 8/2006 | Ralph et al. | |
| 2002/0022847 | A1 * | 2/2002 | Ray et al. | 606/96 |
| 2003/0083667 | A1 * | 5/2003 | Ralph et al. | 606/96 |
| 2005/0015092 | A1 * | 1/2005 | Rathbun et al. | 606/96 |

* cited by examiner

*Primary Examiner* — Thomas Barrett
*Assistant Examiner* — Matthew Lawson
(74) *Attorney, Agent, or Firm* — Carter, DeLuca, Farrell & Schmidt, LLP

(57) ABSTRACT

A drill guide apparatus for aligning a cervical drill bit and a target site in a vertebral body prior to drilling a hole in the vertebral body is disclosed. The apparatus includes a handle assembly, an extension member extending from the handle assembly, a mounting plate disposed on the distal end of the extension member, a guide member proximally extending from the mounting plate and a rotation mechanism operably connecting the handle assembly and the extension member. The rotation mechanism is configured to selectively position the handle assembly relative to the mounting plate. The guide member may include a single or double barrel configuration. The guide member is selectively positionable relative to the mounting plate. The mounting plate may include a protrusion for selectively engaging a second plate.

21 Claims, 9 Drawing Sheets

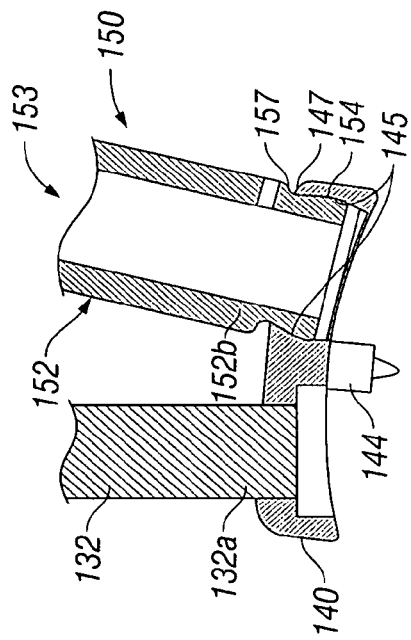
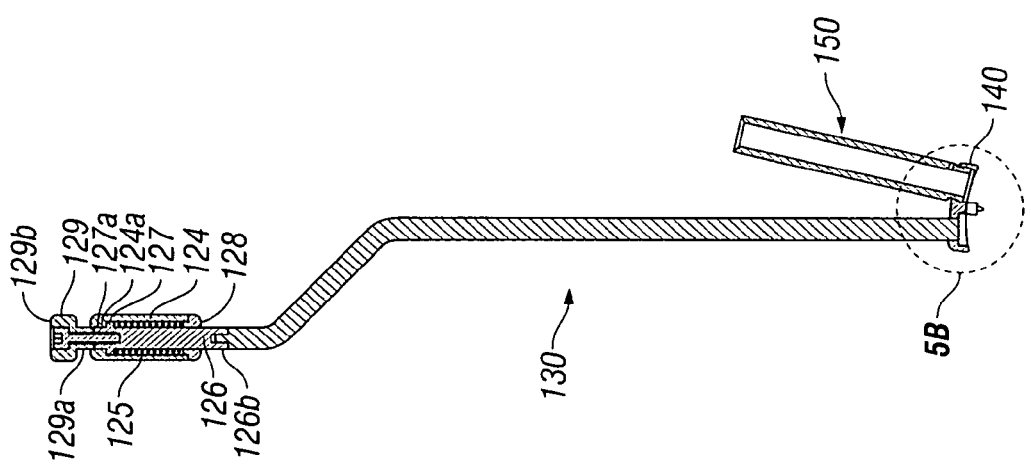

CERVICAL DRILL GUIDE APPARATUS

REFERENCE TO RELATED APPLICATIONS

This application claims priority to, and the benefit of, U.S. Provisional patent application Ser. No. 60/847,593, filed on Sep. 26, 2006, the entire contents are hereby incorporated by reference in their entirety.

BACKGROUND

1. Technical Field

The present disclosure relates generally to orthopedic spinal surgery, and more particularly, to devices, systems, and methods for guiding a cervical drill, bone screw or other instrument during spinal surgery.

2. Background of Related Art

The spinal column is a complex system of bones and connective tissues that provide support for the human body and protection for the spinal cord and nerves. The adult spine is comprised of twenty-four vertebral bodies, which are subdivided into three areas, including seven cervical vertebrae, twelve thoracic vertebrae and five lumbar vertebrae. Between each vertebral body is an intervertebral disc that cushions and dampens the various translational and rotational forces exerted upon the spinal column.

There are various disorders, diseases and types of injury which the spinal column may experience in a lifetime. These problems may include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as a spinal fusion. Spinal fusion involves fusing two or more vertebral bodies together to eliminate motion at the intervertebral disc or joint. To achieve spinal fusion, natural or artificial bone, along with a spacing device, replace part or all of the intervertebral disc to form a rigid column of bone. Mechanical hardware is connected to the adjacent vertebrae to stabilize the spine in that area while the bone grows and the fusion occurs.

The mechanical hardware used to immobilize the spinal column typically involves a series of bone screws and metal rods or plates. When the spine surgery is performed posteriorly, it is common practice to place pedicle bone screws into the vertebral bodies and then connect a metal rod between the screws, thus creating a rigid structure between adjacent vertebral bodies. When the spinal surgery is performed anteriorly, it is common practice to attach a thin metal plate directly to the vertebral bodies and secure it to each vertebral level using one or more bone screws. For the remainder of this disclosure, references to spinal surgery will be referring to the anteriorly performed surgery in which a metal plate is secured directly to the vertebrae using bone screws.

Because the spine is routinely subject to mechanical loads which cycle during movement, a primary concern of physicians performing metal plate implantation surgeries, as well as of the patients in whom the implants are placed, is the risk of screw pullout. This is of particular concern in the cervical region because of the critical vessels that abut the anterior surfaces of the cervical spine. Screw pullout occurs when the cylindrical portion of the bone that surrounds the inserted screw fails. A bone screw that is implanted into the vertebrae perpendicular to the plate is particularly weak because the region of the bone that must fail for pullout to occur is only as large as the outer diameter of the screw threads. Screws which are angled inward towards one another, also referred to as "toe-nailed", or ones which diverge within the bone have been found to greatly reduce the likelihood of screw pull out because the region of bone that must fail is increased as compared to that of screws implanted perpendicular to the plate.

The metal plates used to connect the vertebrae in spinal surgery are well known in the art. These plates may define any number of openings configured for receiving bone screws. The openings for receiving the screws may include a beveled or angled edge for more securely receiving the angled screws. The metal plates may also include openings or grooves for releasably receiving an elongated handle member for maintaining the metal plate during implantation. Because the metal plates used in spinal fusion are relatively small and awkward to handle, elongated handle members have been developed for releasably engaging the metal plates such that they may be held in position while the bone screws are being applied. The elongated handle members generally include a handle assembly for grasping the handle member and an extension member connected thereto. The distal end of the extension member may include any number of clips, protrusions, tabs or the like for releasably engaging the metal plate.

As discussed above, positioning of the bone screws used to secure the metal plate to the vertebrae is important to preventing screw pullout, and thus a successful spinal fusion. The elongated handle members may further be configured to include a guide member for guiding the drill, screws or other instrument for assisting a surgeon in positioning the bone screws during implantation of the metal plate. Commonly owned U.S. Pat. No. 7,094,242 to Ralph et al., discloses such a device, and is incorporated herein by reference in its entirety.

Conventional drill guides generally include a handle assembly fixedly attached to the proximal end of an extension member. The distal end of the extension member generally includes a mounting assembly configured for releasable engagement with a metal plate. The extension member may be configured to include one or more guide members. Alternative drill guides include a guide member that is independently attached to the mounting assembly. During procedures involving surgeons with different preferences, more than one surgeon or the use of multiple instruments within the surgical field, the handle assembly of the drill guide often is oriented in a less than convenient position. Because the handle assembly is fixedly attached to the extension member, the orientation of the handle assembly cannot be adjusted. Furthermore, because the handle is fixedly attached to the extension member it cannot be removed, and thus, cannot be replaced. In the event that the handle assembly becomes worn or damaged, the only option is to replace the entire drill guide.

Therefore, it would be beneficial to have a drill guide apparatus including a handle assembly that can be selectively positioned about an extension member prior to or during implantation of a metal plate. It would further be beneficial to have a handle assembly that can be removed from the extension member.

SUMMARY

A drill guide apparatus for aligning a cervical drill bit and a target site in a vertebral body prior to drilling a hole in the vertebral body is provided. According to a first embodiment, the apparatus includes a handle assembly, an extension member extending from the handle assembly, a mounting plate disposed on the distal end of the extension member, a guide member extending proximally from the mounting plate and a rotation mechanism operationally connecting the handle assembly and the extension member.

The rotation mechanism is configured to permit the handle assembly to be selectively positioned relative to the mounting plate. The handle assembly and mounting plate remain generally parallel throughout the positioning of the handle assembly relative to the mounting plate.

The guide member may be of a single barrel variety, or may instead include a double barrel configuration. The first and/or second barrels define longitudinal bores configured to receive the operational end of an instrument. The first and/or second barrels may be selectively positionable relative to the base and independent of one another.

The mounting plate may include a protrusion extending distally therefrom. The protrusion may be configured for selective engagement with a second plate. The protrusions may be configured for friction fit with the second plate.

According to another embodiment of the disclosure, a drill guide apparatus includes a handle assembly, an extension member extending from the handle, a mounting plate disposed on a distal end of the extension member and a guide member extending proximally of the mounting plate. The guide member includes a double barrel configuration. The barrels of the guide member are configured for selective positioning relative to the mounting plate and independent of on another.

BRIEF DESCRIPTION OF THE DRAWINGS

Embodiments of the presently disclosed cervical drill guide apparatus are described herein with reference to the accompanying drawings, wherein:

FIG. 5A is a side cross-sectional view of the guide apparatus of FIG. 1;

FIG. 5B is an enlarged view of the region of 5B of FIG. 5A;

DETAILED DESCRIPTION OF THE EMBODIMENTS

While the presently disclosed cervical drill guide apparatus will be described more fully hereinafter with reference to the accompanying drawings, in which particular embodiments are shown, it is to be understood at the outset that persons skilled in the art may modify the apparatus herein described while achieving the functions and results of this apparatus. Accordingly, the descriptions that follow are to be understood as illustrative and exemplary of specific structures, aspects and features within the broad scope of the present disclosure and not as limiting of such broad scope. Like numbers refer to similar features of like elements throughout.

Figure 1:
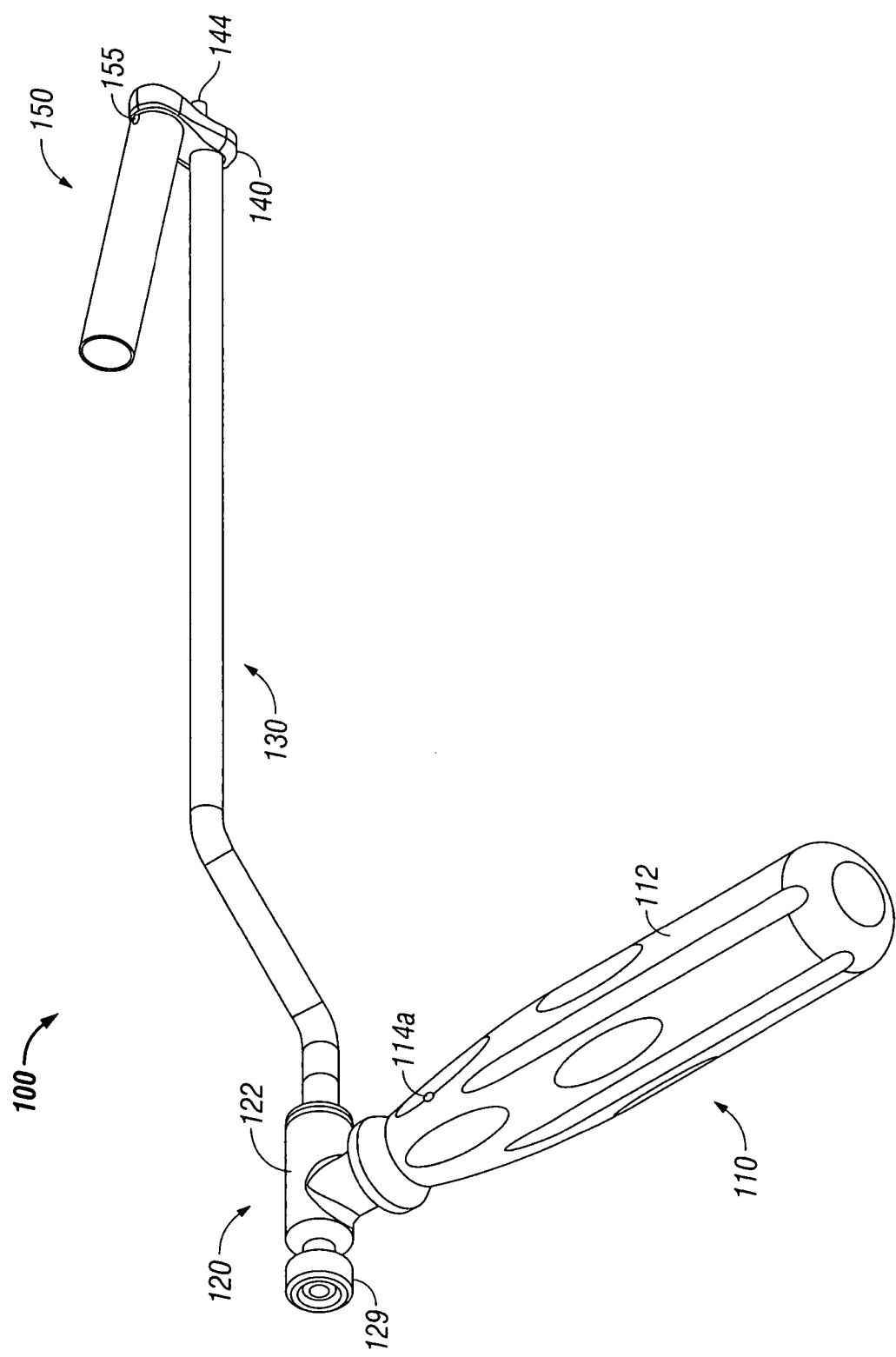
FIG. 1 is an isometric view of an embodiment of the drill guide apparatus of the present disclosure.
Figure 2:
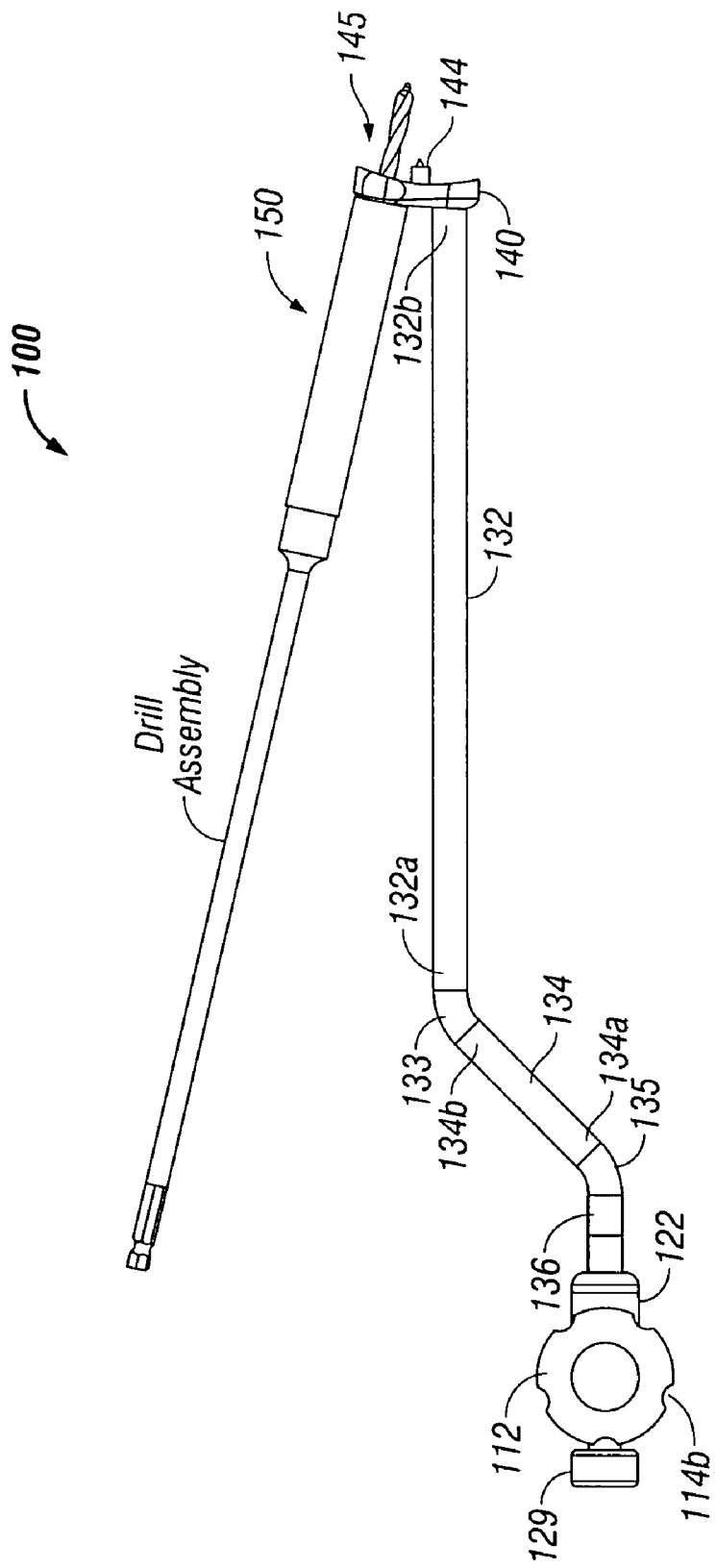
FIG. 2 is a side view of the drill guide apparatus of FIG. 1 including a drill bit assembly.
Figure 3:
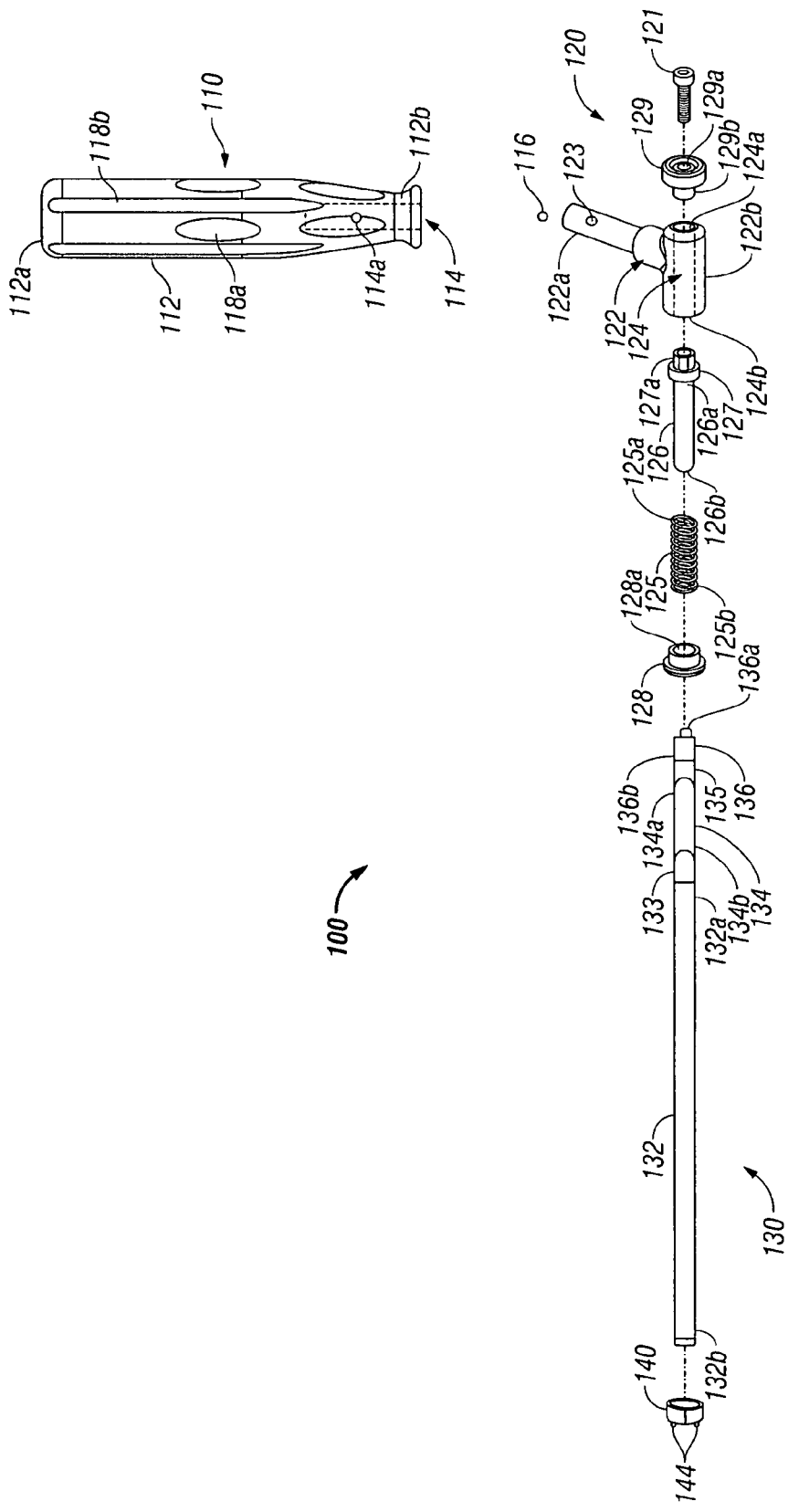
FIG. 3 is an exploded side view of the drill guide assembly of FIGS. 1 and 2.

Referring now to FIGS. 1-3, an embodiment of the present disclosure is shown generally as drill guide 100. Drill guide 100 includes a handle assembly 110, a rotation mechanism 120, an extension member 130, a mounting plate 140 and a guide member 150.

Handle assembly 110 includes a handle 112 having a proximal end 112*a* and a distal end 112*b*. Distal end 112*b* of handle 112 defines a longitudinal bore 114 therein. Longitudinal bore 114 is configured for operable engagement with rotation mechanism 120. Distal end 112*b* of handle assembly 112 further includes an opening 114*a* perpendicularly disposed to longitudinal bore 114 for receiving a locking pin 116. Handle assembly 110 may include any number of configurations to facilitate greater control of drill guide 100 by a surgeon. Handle 112 of handle assembly 110 may include ridges or knurls 118*a* and/or longitudinal grooves 118*b* for facilitating grasping of handle assembly 110. The length and/or diameter of handle 112 may be modified to accommodate the preferences of the surgeon performing the procedure. Handle 112 may further include finger holes or guards, a slip free coating or the like for improving the user interface with drill guide 100.

Referring now to FIG. 3, rotation mechanism 120 operably connects handle assembly 110 with extension member 130. Rotation mechanism 120 includes a connection member 122, a spring means or spring 125, a shaft member 126, proximal and distal end caps 127, 128, respectively, and a screw 121. Connection member 122 includes a proximal end 122*a* and a distal end 122*b*. Proximal end 122*a* of connection member 122 is configured to be received within longitudinal through bore 114 defined by distal end 112*b* of handle 112. Proximal end 122*a* of connection member 122 defines an opening 123 configured for aligning with opening 114*a* formed in distal end 112*b* of handle 112 when proximal end 122*a* of connection member 122 is completely received within through bore 114 of handle 112. Opening 123 is sized to receive locking pin 116.

When proximal end 122*a* of connection member 122 is received within through bore 114, opening 114*a* formed in connection member 122 and opening 123 formed in handle 112 may be aligned and locking pin 116 may be received therethrough for securely affixing handle assembly 110 to adjustment mechanism 120. Removal of locking pin 116 from within openings 114*a* and 123 permits handle assembly 110 to be removed from connection member 122. In this manner, handle assembly 110 of drill guide 100 may be removed and, if warranted because of failure or user preference, may be replaced. In an alternate embodiment, handle assembly 110 may be frictional received or snap fit about connection member 122. In yet another embodiment, handle assembly 110 may be rotatably mounted about connection member 122.

Distal end 122*b* of connection member 122 defines a through bore 124. Through bore 124 is perpendicularly aligned with proximal end 122*a* of connection member 122. Through bore 124 is generally cylindrical and is defined by an open distal end 124*b* and a partially closed proximal end 124*a* having a female hex shaped configuration. Through bore 124 is sized to receive spring 125 positioned about shaft member 126. Shaft member 126 is a substantial cylindrical elongated member having a proximal end 126*a* and a distal end 126*b*. Distal end 126*b* of shaft member 126 is configured to be received within spring 125, yet is narrow enough to be slidably and rotatably disposed within through bore 124. Proximal end 126*a* of shaft member 126 includes a collar 127 having a diameter larger than that of distal end 126b. Collar 127 is of a sufficient size such that it will retain spring 125 about shaft member 126. Proximal end 126a of shaft member 126 further includes geared portion 127a extending beyond collar 127. Geared portion 127a may have a cross-section of a number of shapes, including but not limited to, square, diamond, pentagon, hexagon, and multi-pointed star.

Partially closed proximal end 124a is configured for engagingly receiving geared portion 127a. Partially closed proximal end 124a may have a cross-section defining an opening (not shown) of any number of shapes, including but not limited to, square, diamond, pentagon, hexagon, and multi-pointed star. The opening formed in partially closed proximal end 124a preferably corresponds in size and configuration with the cross section of geared portion 127 formed on proximal end 126a of shaft member 126. When shaft member 126 is inserted into through bore 124, geared portion 127a is received within partially closed proximal end 124a. Collar 127 formed on distal end 126b retains shaft member 126 within through bore 124 formed in connection member 122.

In particular, shaft member 126 is disposed within through bore 124 such that proximal end 127a is substantially flush with proximal end 124a. The male hex head of proximal end 127a includes a threaded opening for receiving screw 121. The male hex head of proximal end 127a mates with the female hex opening of 124a. Screw 121 threadably couples a proximal end cap 129 to shaft member 126.

Assembly of rotation mechanism 120 requires insertion of shaft member 126 into through bore 124 such that gear portion 127a is received in the opening formed in partially closed proximal end 124a. Collar 127 abuts partially closed proximal end 124a and prevents passage of shaft member 126 therethrough. Spring 125 is disposed about distal end 126b of shaft member 126 and is also received within through bore 124. Spring 125 includes a proximal end 125a and a distal end 125b. Proximal end 125a of spring 125 abuts collar 127 of shaft member 126. Spring 125, and thus shaft member 126 by virtue of its position in relation to spring 125 is retained within through bore 124 formed in distal end 122b of connection member 122 by distal end cap 128.

Distal end cap 128 defines an opening 128a therethrough sized to permit the passage of distal end 126b of shaft member 126 therethrough. Distal end cap 128 is configured to be received about a portion of distal end 126b of shaft member 126 that extends beyond open distal end 124b of through bore 124. Distal end cap 128 is frictionally received within open distal end 124b of through bore 124. Distal end cap 128 is further configured to abut distal end 125b of spring 125. Because spring 125 is secured within through bore 124 by collar 127 formed on shaft member 126 and distal end cap 128, shaft member 126 is thereby springedly retained within through bore 124. In an alternate embodiment distal end cap 128 may be secured within open distal end 124b of through bore 124 using any conventional means, including but not limited to adhesives, welds, crimping, mechanical fasteners and the like. In an alternate embodiment spring means 125 may instead comprise a hydraulic or pneumatic actuator for springedly biasing shaft member 126.

Still referring to FIG. 3, proximal end cap 129 is positioned adjacent geared portion 127a of shaft member 126 while shaft member 126 is retained within through bore 124. Proximal end cap 129 is secured to shaft member 126 with screw 121. In an alternate embodiment proximal end cap 129 may be secured to shaft member 126 using adhesive, welds, snap-fit fasteners or the like. Proximal end cap 129 includes a proximal end 129a and a distal end 129b. Distal end 129b of proximal end cap 129 forms a button-like assembly that extends distally towards shaft member 126. The button-like assembly of distal end 129b cooperates with shaft member 126 and biases proximal end cap 129 towards partially closed proximal end 124a of through bore 124. Proximal end 129a of proximal end cap 129 is configured with a diameter sufficiently small to be rotatably received within partially closed proximal end 124a of through bore 124.

Proximal end 129a of proximal end cap 129 is further configured such that when button-like assembly formed in distal end 129b of proximal end cap 129 is depressed, geared portion 127 of shaft member 126 is displaced from within partially open proximal end 124a of through bore 124 and shaft member 126 is moved distally such that the male hex head of proximal end 127a and the female hex opening 124a are disengaged, thereby allowing handle 110 to rotate about a longitudinal axis of shaft member 126. In this manner handle assembly 110 may be freely rotated about shaft member 126. Handle assembly 110 and connection mechanism 120 may be configured such that depression of proximal end 129a of proximal end cap 129 can be completed with one hand. Depression of proximal end 129a of proximal end cap 129 causes the compression of spring 125 within through bore 124. When the depression force is released, geared portion 127a of shaft member 126 is springedly returned to within the opening formed in partially open proximal end 124a of through bore 124. In this manner, shaft member 126 is once again prevented from freely rotating within through bore 124. The position of handle assembly 110 relative to shaft member 126 is limited by the configuration of geared portion 127a and partially closed proximal end 124a defining through bore 124. Distal end 126b of shaft member 126 is further configured for secure attachment to extension member 130.

Extension member 130 is configured for connecting rotating mechanism 120, including handle assembly 110, with mounting plate 140. Extension member 130 includes a first extension member 132, a second extension member 134, and a third extension member 136. First, second and third extension members 132, 134, 136 each have a proximal end 132a, 134a, 136a and a distal end 132b, 134b, 136b, respectively. Proximal end 132a of first extension member 132 is securely connected to distal end 134b of second extension member 134 at a first joint 133. Proximal end 134a of second extension member 134 is securely connected to distal end 136b of the third extension member 136 at a second joint 135. First and second joints 133, 135 are configured such that when cervical drill guide 100 is assembled first extension member 132 is aligned parallel with shaft member 126. Fixedly attached to distal end 132b of first extension member 132 is mounting plate 140.

Mounting plate 140 is a substantially flat member configured to releasably connecting a metal plate (not shown) with drill guide 100. Mounting plate 140 may be securely affixed to distal end 132b of first extension member 132 with any known means, including but not limited to, adhesive, mechanical fasteners, welding, crimping, friction fit or the like. Mounting plate 140 is affixed perpendicular to first extension member 132. Mounting plate 140 includes one or more protrusions or tabs 144 configured for releasably engaging a metal plate. Protrusions 144 may vary in number, size and location depending on the configuration of the metal plate being implanted. Mounting plate 140 further includes an opening 145 (FIG. 2) configured for receiving guide member 150 (FIG. 4).

Figure 4:
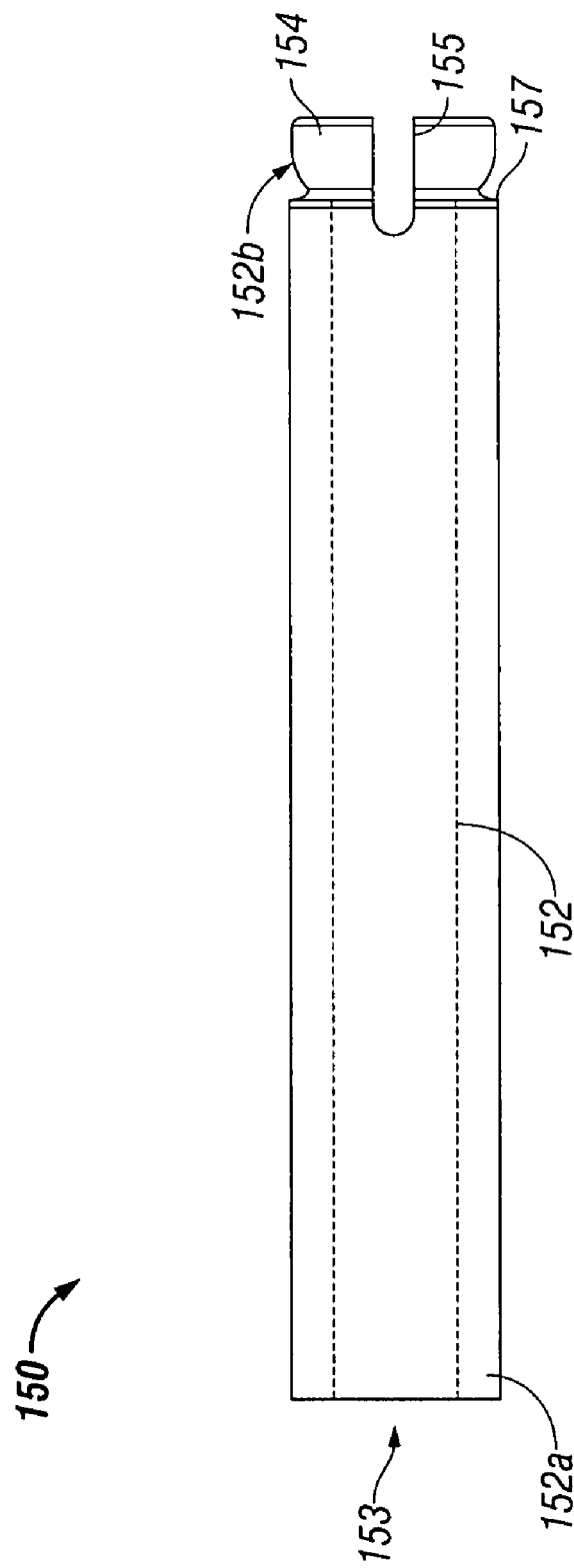
FIG. 4 is an enlarged side view of the guide member of FIGS. 1 and 2.
Figure 6A:
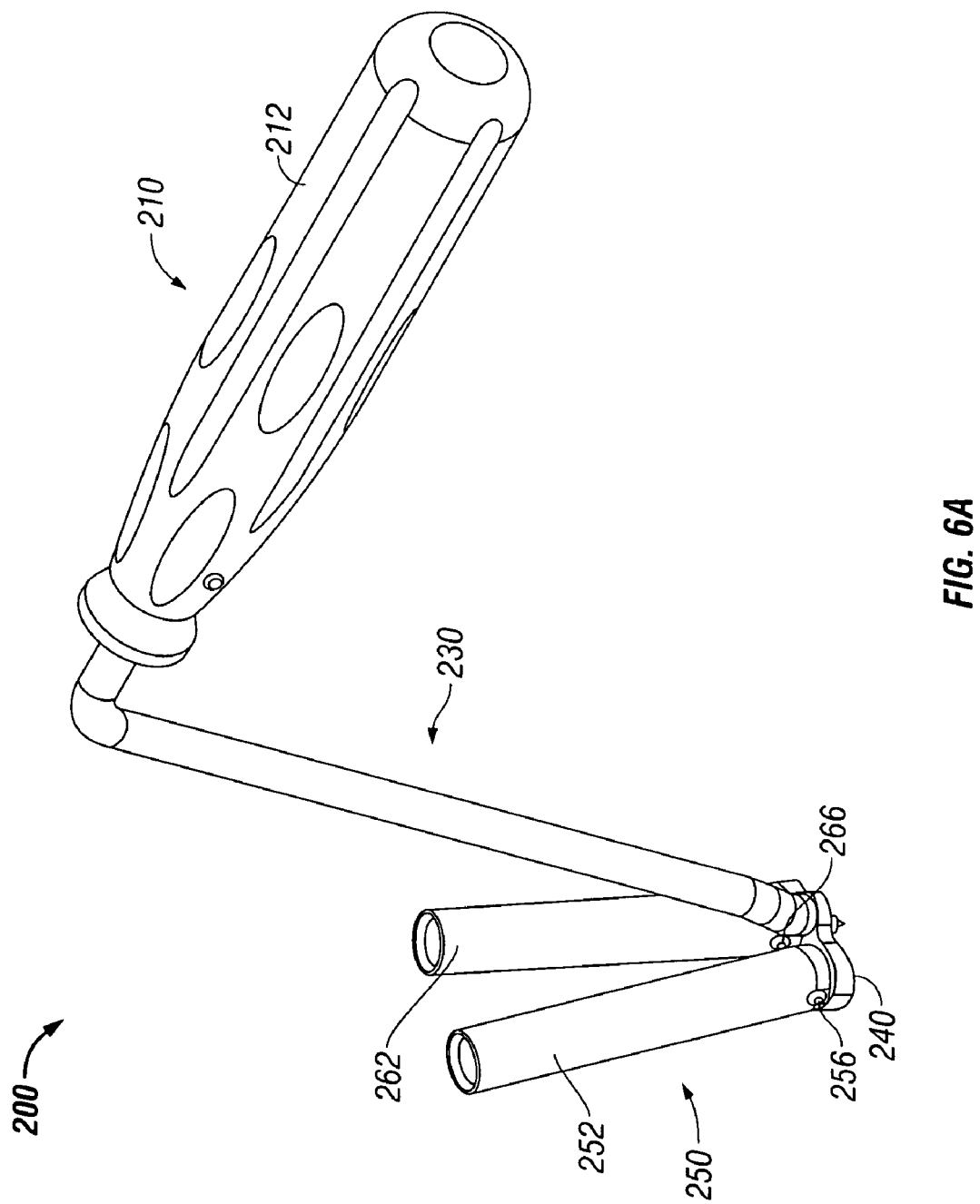
FIG. 6A is a perspective/isometric view of another embodiment of a drill guide according to the present disclosure.
Figure 6B:
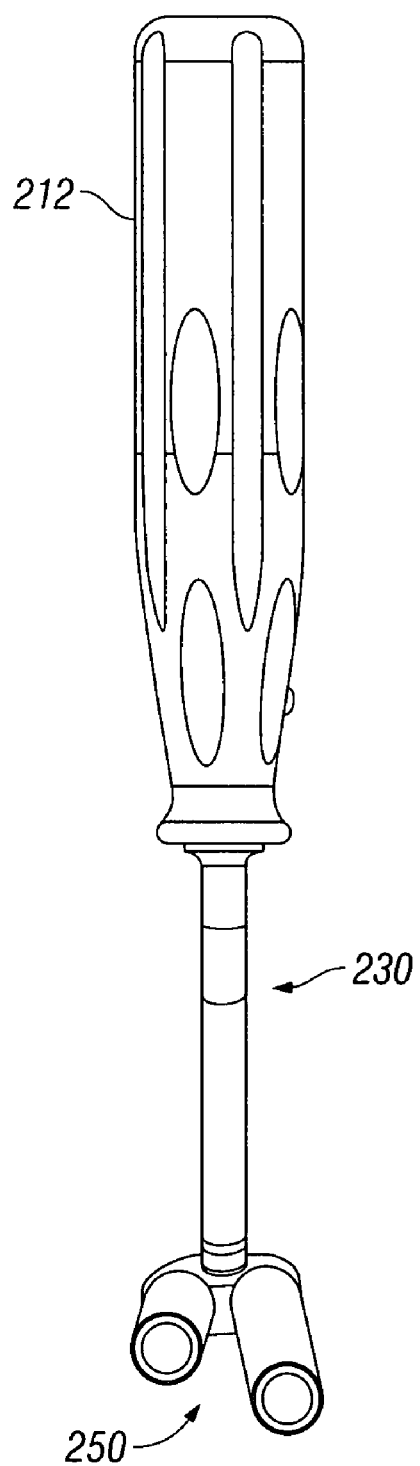
FIG. 6B is a top view of the drill guide apparatus of FIG. 6A.
Figure 6C:
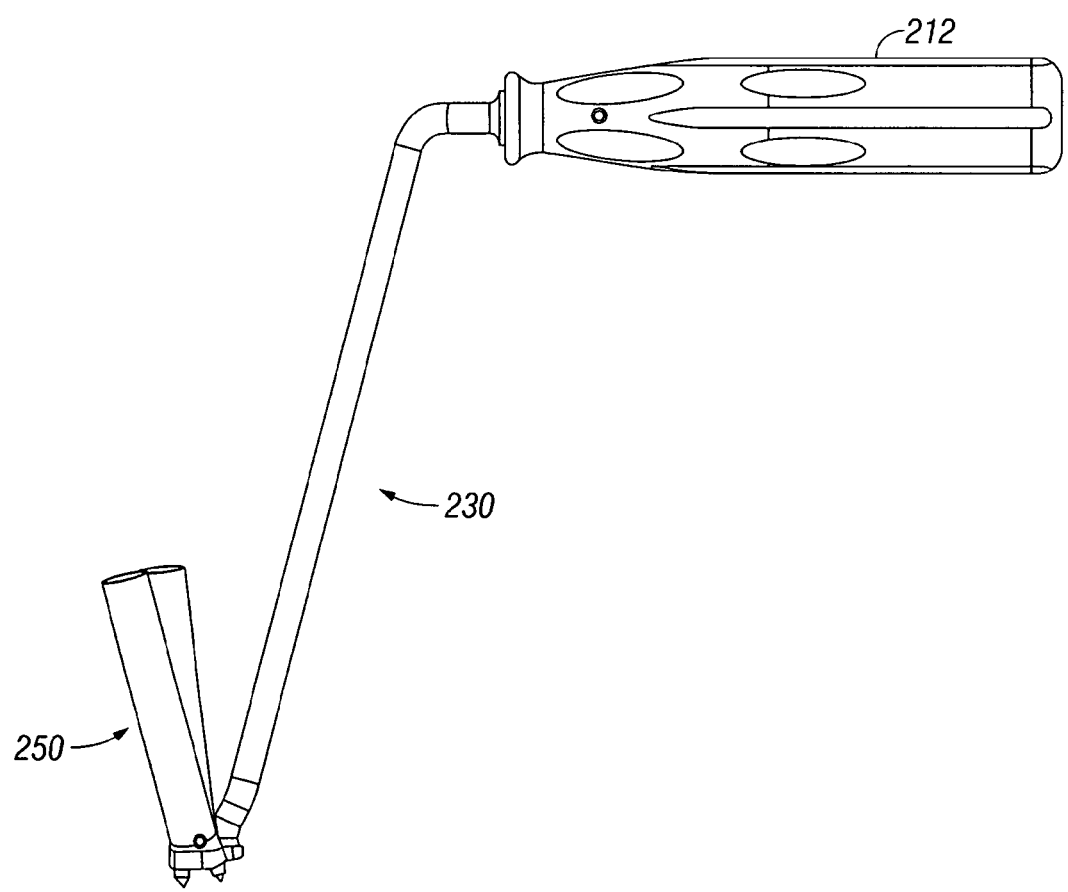
FIG. 6C is a side view of the drill guide apparatus of FIG. 6A.
Figure 6D:
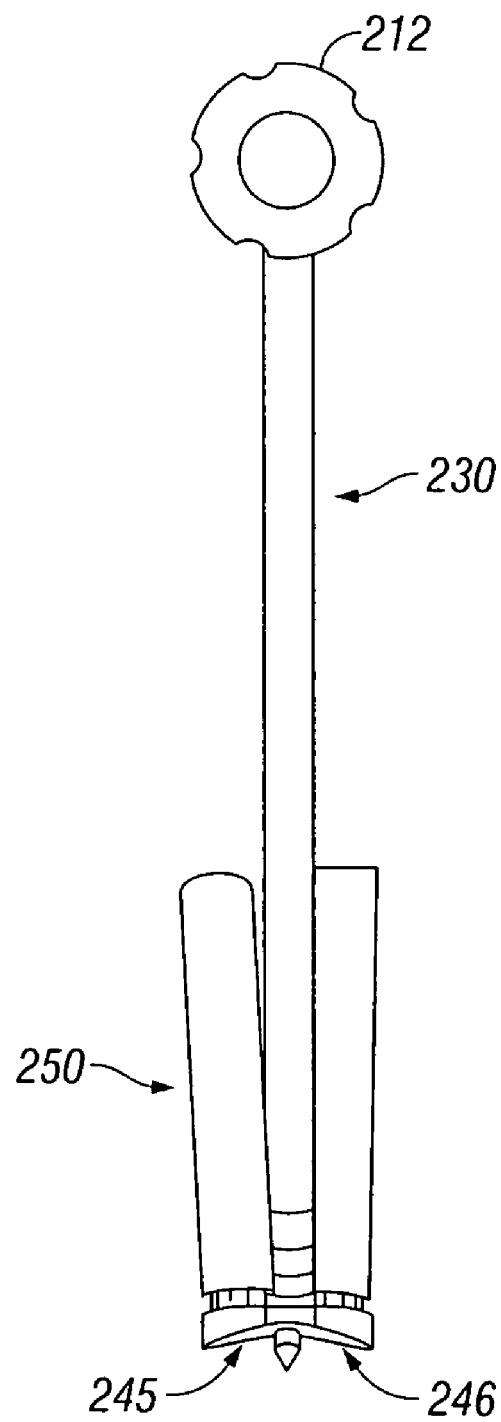
FIG. 6D is a rear view of the drill guide apparatus of FIG. 6A.

Referring now to FIG. 4, guide member 150 includes a tubular member 152 forming a substantially cylindrical member having a proximal end 152a and a distal end 152b. Tubular member 152 includes a longitudinal bore 153 extending therethrough and having a diameter sized to accommodate a drill bit, bone screw or other instrument used during the spinal fusion procedure. Distal end 152b of tubular member 152 forms a semi-spherical outer surface portion 154 configured for being rotatably mounted within in socket 145 of mounting plate 140. In this manner, tubular member 152, and consequently longitudinal bore 153, may be positioned at a plurality of angles with respect to mounting plate 140.

With reference to FIG. 2, mounting plate 140 includes a curvate socket 145 for receiving semi-spherical outer surface portion 154 of distal end 152b of tubular member 152 includes. The walls of socket 145 of mounting plate 140 may have a curvature that matches the contour of the semi-spherical outer surface portion 154. However, it has been contemplated that in other embodiments, walls of another type may be used, such as, for example, walls without a curvature and walls having a different curvature.

Referring still to FIGS. 5A and 5B, semi-spherical outer surface portion 154 may be placed into and removed from within socket 145. Semi-spherical outer surface portion 154 is formed with a notch 155 (FIG. 4) that permits distal end 152b to be radially compressed under pressure. This compression causes a reduction in the diameter of distal end 152b sufficient to permit semi-spherical outer surface portion 154 to be passed into curvate socket 145. Once the pressure is released, semi-spherical outer surface portion 154 returns to its resting diameter, and thereby is secured within curvate socket 145. The configuration of curvate socket 145 and semi-spherical outer surface portion 154 enables guide member 150 to be pivotably and/or rotatably adjusted relative to mounting plate 140. Semi-spherical outer surface portion 154 of base 152 may be removed from within curvate socket 145 of mounting plate 140 by applying a force to the face of distal end 152b of base 152. The top surface of mounting plate 140 may be cut on a radius or angle such that when base 152 is connected therewith base 152 includes a "stop" feature. End 152b defines a transition 157 from cylindrical to spherical. Transition 157 is configured to provide the stop. Modification of the transition may change the amount of angulation base 152 may be permitted to move through.

Alternately configured guide members may be interchangeably secured within curvate socket 145 depending on the procedure being performed and the instruments needed to complete the procedure. In an alternate embodiment, distal end 152b of tubular member 152 does not include notch 155. In this manner guide member 150 is securely affixed to mounting plate 140 at a predetermined angle and, thus, cannot be adjusted, rotated or removed.

With reference to FIGS. 1 and 2, when assembled connecting member 120 and extension member 130 are configured such that handle assembly 110 extends in a plane parallel to the horizontal plane defined by mounting plate 140. Handle assembly 110 and connecting member 120 are further configured such that when button-like distal end 129b of proximal end cap 129 is depressed handle assembly 110 may be freely rotated about extension member 120 within the same parallel plane.

Referring now to FIGS. 6A-6D, an alternate embodiment of the drill guide apparatus of the present disclosure is shown generally as drill guide 200. Drill guide 200 is substantially similar to above disclosed drill guide 100. Drill guide 200 includes a handle assembly 210 having a handle 212, an elongated shaft member 230, a mounting plate 240 and a double-barrel guide member 250. Guide member 250 includes a first tubular member 252 and a second tubular member 262. First and second tubular members 252, 262 are substantially similar to tubular member 152 disclosed hereinabove. First and second tubular members 252, 262 each have a proximal end 252a, 262a and distal end 252b, 262b, respectively. Distal ends 252b, 262b of bases 252, 262 are configured for independent attachment to mounting plate 240.

Mounting plate 240 defines two openings 245, 246 configured for receiving the distal ends 252b, 262b of tubular members 252, 262. Like tubular member 152 of guide member 150, tubular members 252, 262 may include distal ends 252b, 262b having semi-spherical outer surfaces, including a notch, for permitting rotation within openings 245, 246 formed within mounting plate 240. In an alternate embodiment distal ends 252b, 262b of tubular members 252,262 do not include a notch and are, therefore securely affixed to mounting plate 240. In this manner, tubular members 252, 262 may be securely affixed to mounting plate 240 at any predetermined angle. Drill guide 200 may further include a connecting member for selectively rotating handle assembly 210 about extension member 230.

While there has been described and illustrated specific embodiments of the drill guide apparatus, it will be apparent to those skilled in the art that variations and modifications are possible without deviating from the broad spirit and principle of the present disclosure. Therefore, this disclosure shall not be limited to the specific embodiments discussed herein.

What is claimed is:

1. A drill guide apparatus comprising:
    a handle assembly;
    an extension member extending from the handle assembly;
    a mounting plate disposed on a distal end of the extension member, wherein the mounting plate includes a curvate socket extending between a first bone plate contacting surface and an opposed second surface of the mounting plate, wherein the first and second surfaces of the mounting plate are substantially parallel;
    a protrusion extending distally from the mounting plate configured for selective engagement with a vertebral plate, wherein the protrusion is laterally offset from the curvate socket;
    a guide member extending proximally from the mounting plate and defining a longitudinal axis, the guide member including a cylindrical portion and a semi-spherical outer surface portion, the semi-spherical outer surface portion is rotatably mounted within the curvate socket formed in the mounting plate such that the guide member may be positioned at a plurality of angles relative to the mounting plate, wherein the guide member includes a transition between the cylindrical portion and the semi-spherical portion, wherein engagement of the transition with the second surface of the mounting plate limits the angle between the guide member and the mounting plate; and
    a rotation mechanism operably connecting the extension member and the handle assembly, the rotation mechanism configured to selectively position the handle assembly relative to the mounting plate.

2. The drill guide apparatus according to claim 1 wherein the handle assembly is maintained parallel to the mounting plate.

3. The drill guide apparatus according to claim 1 wherein the handle assembly is selectively positionable in predetermined positions relative to the mounting plate.

4. The drill guide apparatus according to claim 1 wherein the guide member defines a longitudinal bore configured for receiving an instrument.

5. The drill guide apparatus according to claim 1 wherein the guide member includes a single tubular member.

6. The drill guide apparatus according to claim 1 wherein the guide member includes first and second tubular members.

7. The drill guide apparatus according to claim 6 wherein the first tubular member is selectively positionable independent of the second tubular member.

8. The drill guide apparatus according to claim 1 wherein the mounting plate is configured to selectively engage a second plate.

9. The drill guide apparatus according to claim 1 wherein the mounting plate includes at least one protrusion for selective engagement with a second plate.

10. The drill guide according to claim 1, wherein the mounting plate has a depth substantially the same as the length of the semi-spherical outer surface portion.

11. The drill guide according to claim 1, wherein the mounting plate includes a second laterally offset protrusion configured for selective engagement with a vertebral plate.

12. The drill guide according to claim 1, wherein the transition extends substantially perpendicular to the longitudinal axis of the guide member.

13. A drill guide apparatus comprising:
a handle assembly;
an extension member extending from the handle assembly;
a mounting plate disposed on a distal end of the extension member, wherein the mounting plate includes a curvate socket extending between a first bone plate contacting surface and an opposed second surface of the mounting plate, wherein the first and second surfaces of the mounting plate are substantially parallel;
a protrusion extending distally from the mounting plate configured for selective engagement with a vertebral plate, wherein the protrusion is laterally offset from the curvate socket; and
a guide mechanism extending proximally from the mounting plate and defining a longitudinal axis, the guide mechanism includes a first tubular member defining a first longitudinal bore and a second tubular member defining a second longitudinal bore, wherein the first and second tubular members each include a cylindrical portion and a semi-spherical outer surface portion, the semi-spherical outer surface portion being rotatably mounted within the curvate socket formed in the mounting plate such that each tubular member may be positioned at a plurality of angles relative to the mounting plate, wherein each of the first and second tubular members includes a transition between the cylindrical portion and the semi-spherical portion, wherein engagement of the transition of each of the first and second tubular members with the second surface of the mounting plate limits the angle between each of the first and second tubular members and the mounting plate.

14. The drill guide according to claim 13 wherein the first tubular member is selectively positionable independent of the second tubular member.

15. The drill guide according to claim 13 wherein the mounting plate is maintained in a parallel relationship with the handle assembly.

16. The drill guide according to claim 13 wherein the mounting plate is configured to selectively engage a second plate.

17. The drill guide according to claim 13 wherein the mounting plate includes at least one protrusion configured for selective engagement with a second plate.

18. The drill guide according to claim 13, wherein the first and second surfaces of the mounting plate are substantially parallel.

19. The drill guide according to claim 13, wherein the mounting plate has a depth substantially the same as the length of the semi-spherical outer surface portion.

20. The drill guide according to claim 13, wherein the mounting plate includes a second laterally offset protrusion configured for selective engagement with a vertebral plate.

21. The drill guide according to claim 13, wherein the transition extends substantially perpendicular to the longitudinal axis of the guide member.

* * * * *